United States Patent [19]

Welsh et al.

[11] Patent Number: 4,632,957
[45] Date of Patent: Dec. 30, 1986

[54] ETHYLENICALLY UNSATURATED ETHYLENE AND PROPYLENE UREAS CONTAINING ALKYLENE UREA GROUPS OR ALKYLENE URETHANE GROUPS, USEFUL IN COATING COMPOSITIONS

[75] Inventors: David A. Welsh, Monroeville; Rostyslaw Dowbenko, Gibsonia, both of Pa.

[73] Assignee: PPG Industries, Inc., Pittsburgh, Pa.

[21] Appl. No.: 646,733

[22] Filed: Sep. 4, 1984

[51] Int. Cl.$^4$ .................. C07D 233/34; C07D 239/10; C08L 31/06
[52] U.S. Cl. ................................... 524/548; 526/263; 548/320; 544/316
[58] Field of Search ......................... 548/320; 544/316; 526/263; 524/548

[56] References Cited

U.S. PATENT DOCUMENTS

| | | | |
|---|---|---|---|
| 2,831,833 | 4/1958 | Aycock et al. | 548/320 |
| 2,881,155 | 4/1959 | Hankins | 548/320 |
| 2,881,171 | 4/1959 | Hankins | 548/320 |
| 2,980,652 | 4/1961 | Melamed et al. | 548/320 |
| 3,300,429 | 1/1967 | Glavis et al. | 548/320 |
| 4,111,877 | 9/1978 | Dixon et al. | 544/267 |
| 4,314,067 | 2/1982 | Herman et al. | 548/320 |
| 4,319,032 | 3/1982 | Sandri et al. | 548/320 |
| 4,340,743 | 7/1982 | Sandri et al. | 548/318 |
| 4,429,095 | 1/1984 | Sandri et al. | 526/263 |

OTHER PUBLICATIONS

Morrison & Boyd, *Organic Chemistry*, 4th Edit., 1983, p. 844.

*Primary Examiner*—Richard A. Schwartz
*Assistant Examiner*—Kurt G. Briscoe
*Attorney, Agent, or Firm*—Barbara J. Park

[57] ABSTRACT

Disclosed is a compound having the formula:

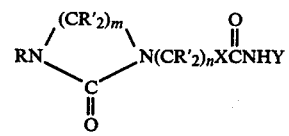

wherein
m is two or three;
n is an integer from one to four;
R is selected from the group consisting of:
  alkyl having one to six carbon atoms,
  hydrogen,
  HOCH$_2$—and
  R"O(CH$_2$)$_a$—, wherein a is an integer from one to six and
  R" is alkyl having 1 to 6 carbon atoms;
each R' in each CR'$_2$ unit of the (CR'$_2$)$_m$ group and of the (CR'$_2$)$_n$ group is independently selected from the group consisting of —H and alkyl having one to four carbon atoms;
X is selected from the group consisting of —O— and

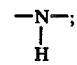

and
Y is a free radical polymerizable unsaturated moiety.

Also disclosed are a process for preparing the compound, latexes containing the compound and coating compositions containing the compound.

11 Claims, No Drawings

ETHYLENICALLY UNSATURATED ETHYLENE AND PROPYLENE UREAS CONTAINING ALKYLENE UREA GROUPS OR ALKYLENE URETHANE GROUPS, USEFUL IN COATING COMPOSITIONS

BACKGROUND OF THE INVENTION

1. Field of the Invention

This invention relates to specific substituted imidazolidone compounds, a process for making the compounds, a process for making latexes containing the compounds and a process for making coating compositions containing the latexes.

2. Description of the Prior Art

Some of the problems industry has faced with latex coatings relate to substrate adhesion. After the latex coating has formed a film on the substrate, the adhesion of the latex coatings to a substrate under conditions of high humidity is a particular problem. The adherence of latex coatings over gloss and semi-gloss substrates is yet another problem. A purpose of this invention is to overcome problems associated with adhesion of latex coating compositions to substrates in high humidity by providing new adhesion promotion monomers. Another purpose is to provide a new process for making such adhesion promoting monomers.

SUMMARY OF THE INVENTION

Compounds have been discovered having the formula:

$$\underset{RN}{\overset{(CR'_2)_m}{\diagup}}\underset{\underset{O}{\overset{\|}{C}}}{\diagdown}N(CR'_2)_n X \overset{O}{\overset{\|}{C}} NHY \quad (I)$$

wherein
m is two or three,
n is an integer from one to four,
R is selected from the group consisting of:
  alkyl having one to six carbon atoms,
  H—,
  HOCH$_2$— and
  R″O(CH$_2$)$_a$— wherein a is an integer from one to six, and R″ is alkyl having 1 to 6 carbon atoms;
each R′ in each CR′$_2$ unit of the (CR′$_2$)m group and of the (CR′$_2$)$_n$ group is independently selected from the group consisting of H— and alkyl having one to one to four carbon atoms;
X is selected from the group consisting of —O— and $$-\underset{\underset{H}{|}}{N}-;$$

and
Y is a free radical polymerizable unsaturated moiety selected from the group consisting of:
  (meth)acrylic-containing monoisocyanate residues, preferably $$-(CH_2)_q O\overset{O}{\overset{\|}{C}}\underset{\underset{R'''}{|}}{C}=CH_2 \quad (III)$$

styrene-containing monoisocyanate residues, preferably $$\underset{H_3C\overset{|}{C}CH_3}{\phantom{X}}\phantom{XXX} (IV)$$

$$\begin{array}{c}\text{benzene ring}\end{array}-\underset{\underset{R'''}{|}}{C}=CH_2$$

maleic and fumaric type monoisocyanate residues, preferably $$-CH_2CH_2O\overset{O}{\overset{\|}{C}}\underset{\underset{R'''}{|}}{C}=\underset{\underset{R'''}{|}}{C}\overset{O}{\overset{\|}{C}}OCH_2CH_3 \quad (V)$$

wherein q is an integer from two to four and R‴ is selected from the group consisting of —H and —CH$_3$.

These compounds when copolymerized with monomers provide latexes having improved adhesion in high humidity.

DESCRIPTION OF THE PREFERRED EMBODIMENTS

The compounds of the invention are made by the reaction of a primary amine or primary alcohol of the formula:

$$\underset{RN}{\overset{(CR'_2)_m}{\diagup}}\underset{\underset{O}{\overset{\|}{C}}}{\diagdown}N(CR'_2)_n XH \quad (II)$$

wherein R, R′, X, m and n are as previously stated, with a monoisocyanate having ethylenic unsaturation of a formula OCNY wherein Y is an ethylenically unsaturated moiety preferably selected from the group consisting of:

$$-(CH_2)_q O\overset{O}{\overset{\|}{C}}\underset{\underset{R'''}{|}}{C}=CH_2, \quad (III)$$

$$\underset{H_3C\overset{|}{C}CH_3}{\phantom{X}}\phantom{XXX} (IV)$$

$$\begin{array}{c}\text{benzene ring}\end{array}-\underset{\underset{R'''}{|}}{C}=CH_2 \quad \text{and}$$

$$-CH_2CH_2O\overset{O}{\overset{\|}{C}}\underset{\underset{R'''}{|}}{C}=\underset{\underset{R'''}{|}}{C}\overset{O}{\overset{\|}{C}}OCH_2CH_3 \quad (V)$$

wherein q and R‴ are as previously stated.

Preferred useful primary amines of formula (II) include 1-(beta-aminoalkyl)-2-imidazolidones wherein the alkyl group is defined to be the $(CR'_2)_n$ moiety of formula (II), i.e. a subset of the set of $C_xR'_{2x+2}$ with 2 hydrogens removed. Typical examples of such 1-(beta-aminoalkyl)-2-imidazolidones include 1-(beta-aminoethyl)-2-imidazolidone, 1-(beta-aminopropyl)-2-imidazolidone and 1-(3-amino-2-butyl)-2-imidazolidone. Additional preferred useful primary amines of formula (II) include 1-(beta-aminoalkyl)-3-(alkyl)-2-imidazolidones wherein the alkyl is straight or branched and is represented by the moiety R in formula (II), such as 1-(beta-aminoethyl)-3-(methyl)-2-imidazolidone, 1-(beta-aminoethyl)-3-(ethyl)-2-imidazolidone, 1-(beta-aminoethyl)-3-(propyl)-2-imidazolidone, 1-(beta-aminoethyl)-3-(butyl)-2-imidazolidone, and 1-(beta-aminoethyl)-3-(pentyl)-2-imidazolidone, and 1-(beta-aminoethyl)-3-(hexyl)-2-imidazolidone.

Other useful primary amines include 1-(aminomethyl)-2-imidazolidone, 1-(4-aminobutyl)-2-imidazolidone, 1-(3-amino-1-butyl)-2-imidazolidone and corresponding amines containing the alkyl group R of formula (II).

Additional useful primary amines include those in which the R group is $HOCH_2-$ or $CH_3O(CH_2)_a-$ wherein a is an integer from one to six, such as 1-(beta-aminoethyl)-3-(hydroxysethyl)-2-imidazolidone, and 1-(beta-aminoethyl)-3-(methoxyhexyl)-2-imidazolidone and 1-(aminoethyl)-3-(methoxyethyl)-2-imidazolidone. Preferably R' is selected from the group consisting of —H and —$CH_3$.

Useful primary alcohols of formula (II) include those primary alcohols corresponding to the above-mentioned amines, such as 1-(beta-hydroxyalkyl)-2-imidazolidones wherein the alkyl is defined to be the $(CR'_2)_n$ moiety of formula (II) i.e. a subset of the set of $C_xR_{2x+2}$ with 2 hydrogens removed. Examples of such 1-(beta-hydroxyalkyl)-2-imidazolidones include 1-(beta-hydroxyethyl)-2-imidazolidone, 1-(beta-hydroxypropyl)-2-imidazolidone and 1-(beta-hydroxybutyl)-2-imidazolidone. Additional useful primary alcohols of formula (II) include 1-(beta-hydroxyalkyl)-3-alkyl-2-imidazolidones, such as 1-(beta-hydroxyethyl)-3methyl-2-imidazolidone, 1-(beta-hydroxybutyl)-3-hexyl-2-imidazolidone, 1-(beta-hydroxyethyl)-3-(hydroxymethyl)-2-imidazolidone and 1-(hydroxypropyl)-3-(methoxybutyl)-2-imidazolidone.

The primary amines or primary alcohols are reacted with the monisocyanates containing ethylenic unsaturation to produce the compounds of the invention containing alkylene urea groups or alkylene urethane groups, respectively. The importance of the monoisocyanate is that it contain an isocyanate group and ethylenic unsaturation in such a manner to provide compounds of the invention which are compatible with the polymerization monomers of the latexes of the invention. These monoisocyanates are described herein.

Useful as the monoisocyanates having ethylenically unsaturated moieties include the (meth)acrylic-containing monoisocyanates, preferably having moieties of formula III, the styrene-containing monoisocyanates, preferably, having moieties of formula IV and the maleic or fumaric type monoisocyanates, preferably having moieties of formula V.

Useful as the monoisocyanates having ethylenic unsaturation which are (meth)acrylic-containing monoisocyanates having moieties of formula III include isocyanatoalkyl methacrylates, such as isocyantoethyl methacrylate, isocyanatopropyl methacrylate and isocyanatobutyl methacrylate as well as the corresponding acrylates, isocyanatoethyl acrylate, isocyanatopropyl acrylate and isocyanatobutyl acrylate. The alkyl group of the moiety $(CH_2)_q$ as well as the alkyl group of the hereinafter described isocyanato alkyl in the maleic and fumaric type monoisocyanates having ethylenic unsaturation is actually an alkylene group, i.e, a $C_qH_{2q+2}$ with 2 hydrogens removed, but the terms are used interchangeably herein. Other useful monoisocyanates contain moieties from crotonic acid, such as isocyanatoalkyl crotonates, particularly isocyanatoethyl crotonate.

Useful as the monoisocyanates having ethylenic unsaturation which include styrene-containing monoisocyanates having moieties of formula IV are alpha-methylstyrene-meta-isopropylidene isocyanate and alpha-methylstyrene-para-isopropylidene isocyanate.

Useful as the monoisocyanates having ethylenic unsaturation which are maleic or fumaric type monoisocyanates having moieties of formula V include isocyanato alkyl fumarate and isocyanato alkyl maleate wherein the alkyl has 1 to 4 carbon atoms such as fumaric acid ethyl ester isocyanatoethyl ester and maleic acid ethyl ester isocyanatoethyl ester. Also useful are the monoisocyanate derivatives of itaconic acid corresponding to the above maleates such as itaconic acid ethyl ester isocyanatoethyl ester.

The process for preparation of the compounds of the invention proceeds generally by reacting the primary amine or primary alcohol of formula II in a solvent or diluent for the compound of the invention with the isocyanate, preferably of formulas III, IV or V, at a reaction temperature of from about 40° C. to about 80° C. over a time period of about one hour. Deionized water is then added to the solution to produce a wet adhesion promoting monomer solution of the invention having a solids content of from about 10% to about 50% by weight. The wet adhesion monomer solutions are generally filtered after preparation. The solids content of the monomer solution is not critical and merely provides an easily handled material for the preparation of the latex.

Typical solvents or diluents used in the preparation of the compounds of the invention include toluene and other solvents, which are unreactive with isocyanates, such as the preferred tertiary-butanol.

The latexes of the invention are prepared generally by any suitable process known to those skilled in the art. The compounds of the invention are incorporated into the latex of the invention, preferably by emulsion copolymerization with suitable comonomers and a polymerization catalyst. The preparation of a preferred embodiment, an acrylic latex of the invention, proceeds generally by the following process.

The process involves: (a) preparing a monomer pre-emulsion by (i) feeding a surfactant mix comprising deionized water, anionic surfactant and nonionic surfactants into a pre-emulsification tank, at ambient temperature, under nitrogen blanket with good agitation, (ii) adding a monomer charge comprising the substituted imidazolidone compound of formula I and other useful comonomers to the surfactant mix over a time period of about 0.5 to about 1.0 hour; (b) preparing a seed charge by (i) adding a portion of the monomer pre-emulsion to a reactor charge in a reactor tank, (ii) adding an initiator charge to the monomer pre-emulsion and reactor charge, and (iii) agitating the seed charge at reaction temperature for about one-half hour until the seed charge polymerizes completely; (c) feeding the remainder of the monomer pre-emulsion to the seed charge over a time period of about two hours; and (d) heating the charge at reaction temperature for about one hour to produce the acrylic latex of the invention.

The monomer pre-emulsion comprises the surfactant mix and the monomer charge.

The surfactant mix of the invention comprises deionized water, anionic surfactant and nonionic surfactants.

Typical anionic surfactants useful in preparing the surfactant mix include sodium lauryl sulfate, sodium dodecylbenzene sulfonate and others generally known to those skilled in the art, such as Sipex UB (30) anionic surfactant, which is an aqueous solution of sodium lauryl sulfate 30% active manufactured by Alcolac, Inc.

Typical nonionic surfactants useful in preparing the surfactant mix include ethoxylated nonyl and octyl phenols, propylene oxide-ethylene oxide block copolymers and others generally known to those skilled in the art, particularly ethylene oxide adducts of nonylphenol such as Triton N101, nonionic surfactant, a product of Rohm & Haas and Igepal CO-850, CO-890 and CO-977, nonionic surfactants, products of GAS Corporation.

The monomer charge comprises the substituted imidazolidone compound of formula I and other useful comonomers. Typical comonomers useful in preparing the monomer charge include polymerizable ethylenically unsaturated carboxylic acids. Examples of such unsaturated carboxylic acids include the ethylenically unsaturated carboxylic acids such as acrylic acid, methacrylic acid, maleic acid, fumaric acid, crotonic acid and itaconic acid. Also useful are the half esters of maleic, fumaric and itaconic acids in which one of the carboxyl groups is esterfied with an alcohol, the identity of which is not significant so long as it does not prevent polymerization or preclude the desired utilization of the product. Butyl hydrogen maleate and ethyl hydrogen fumarate are examples. The preferred ethylenically unsaturated carboxylic acids are the alpha-beta ethylenically unsaturated monocarboxylic acids such as acrylic acid and methacrylic acid.

A second group of comonomers useful in preparing the monomer charge includes the alkyl acrylates and alkyl methacrylates wherein the alkyl group contains from about 1 to about 20 carbon atoms, preferably from about 1 to about 8 carbon atoms. These esters include methyl methacrylate, ethyl methacrylate, propyl methacrylate, butyl methacrylate, isobutyl methacrylate, decyl methacrylate, lauryl methacrylate, 2-ethyl hexyl methacrylate, ethyl acrylate, propyl acrylate, butyl acrylate, isobutyl acrylate and 2-ethyl hexyl acrylate. Also useful within the classification are the alicyclic acrylates and methacrylates such as cyclohexyl methacrylate, isobornyl methacrylate and cyclohexyl acrylate. Ethyl acrylate is preferred.

A third group of useful comonomers useful in preparing the monomer charge includes styrenes. As used herein "styrenes" is understood to include styrene and related compounds such as alpha-methyl styrene, p-methylstyrene, halo-substituted styrenes, vinyl toluene and vinyl naphthalene. Styrene is preferred.

A fourth group of comonomers useful in preparing the monomer charge includes vinyl-containing carboxylic acid esters having 2 to 4 carbon atoms in the carboxylic moiety, preferably vinyl acetate.

A fifth group of comonomers useful in preparing the monomer charge includes vinyl-containing amide monomers such as acrylamide.

A sixth group of comonomers useful in preparing the monomer charge includes vinyl halides such as vinyl chloride.

The latex of the invention preferably comprises as comonomers of the substituted imidazolidone compound of the invention, at least one each of the above first three groups, polymerizable ethylenically unsaturated carboxylic acids, alkyl and alicyclic acrylates and methacrylates, and a styrene.

The latex of the invention preferably comprises between 0.1 percent by weight and 10 percent by weight, more preferably 0.4 percent by weight to 2.0 percent, and even more preferably 1.0 percent by weight to 1.5 percent by weight, based on the total weight of the polymerizable comonomers, of the substituted imidazolidone compound of the invention.

The seed charge comprises a portion of the monomer pre-emulsion, the reactor charge and the initiator charge.

The reactor charge comprises deionized water, a buffer, such as sodium or potassium bicarbonate, and a surfactant, such as Sipex UB (30) anionic surfactant.

The initiator charge for the emulsion polymerization by the process of the invention comprises deionized water and the initiator. Useful as initiators are peroxydisulfates such as ammonium peroxydisulfate and redox initiators such as hydrogen peroxide-sodium formaldehyde sulfoxylate. Ammonium peroxydisulfate is preferred.

The latexes prepared according to the process previously described, are then incorporated into the coating compositions of the invention by first making a paste of a surfactant and a pigment. The latex is then added along with additional surfactant, and the process is completed according to known procedures. The formulation of the coating composition is adjusted according to the latex used.

In order to test the usefulness of the compounds of the invention in the latexes of the invention, wet film adhesion evaluations were performed according to the following general procedure. A Leneta scrub panel is prepared by making a drawdown of a standard gloss enamel-alkyd base. The test coating and control are then drawn down using a 3 mil (0.08 mm) blade. The panels are aged either four days at room temperature or 24 hours at room temperature followed by four hours at 60° C. Three crosshatch sections are made, the first using shallow crosshatching at 90° angles, the second having deep crosshatches at 90° angles and the third having 2 razor blade cuts through the test film intersecting at about a 30° angle. After a moist pad has been placed over the scored areas for about 30 seconds to simulate humid conditions, the surface of the panel is wiped dry. A knife peel test is conducted on the 30° angle test section by pulling a knife blade sidewards across the test section and rating the peeling difficulty on a scale of 1 (falls off) to 10 (no peeling). A piece of masking tape is firmly applied to each of the paint films of the other two test sections of each test. The masking tape is then lifted off the crosshatched substrate at an approximate 45° angle with a swift jerking motion of the hand. The tape tests are then rated from 10 (no paint removal) to 0 (complete paint removal). The three tests are then averaged and taken as a percentage which is considered accurate to ±10%.

The following examples will further illustrate the invention. Where not otherwise specified throughout this specification and claims, temperatures are in degrees Centigrade and parts, percentages and proportions are by weight.

WET FILM ADHESION MONOMER

EXAMPLE 1

Reaction of isocyanatoethyl methacrylate (ICEMA) and 1-(beta-aminoethyl)-2-imidazolidone to form a wet film adhesion monomer of the invention was performed as follows.

To a one liter reaction vessel equipped with thermometer, stirrer, and Dean Stark trap with condenser, were charged the following components:

| Components | Parts by Weight |
| --- | --- |
| 1-(beta-aminoethyl)-2-imidazolidone | 50 |
| Toluene | 433.5 |

After reflux to azeotrope any water, the temperature was lowered to 80° C. and one part methyl hydroquinone was added. Over a period of one-half hour 60.1 parts of ICEMA were added dropwise with stirring.

Upon standing, the reaction mixture separated into an upper solvent layer containing toluene and a viscous semi-solid N-methacryloxy-ethylureido-N'-1-ethylene-2-imidazolidone humid film adhesion monomer of the invention on the bottom.

LATEX

EXAMPLE 2

A latex was prepared using the seeding process of the invention containing 2% of the wet adhesion monomer of Example 1 of the invention.

The following were used:

| Reactor Charge | |
| --- | --- |
| Components | Parts |
| Deionized water | 1166.06 |
| Potassium bicarbonate | 2.0 |
| Sipex UB (30)[1] | 6.0 |

[1]Aqueous solution of sodium lauryl sulfate, 30% active, a product of Alcolac, Inc.

| Initiator | |
| --- | --- |
| Components | Parts |
| Ammonium Peroxydisulfate | 6.46 |
| Deionized water | 37.39 |

| Surfactant Mix | |
| --- | --- |
| Components | Parts |
| Deionized water | 729.74 |
| Sipex U (30) | 22.83 |
| Triton N 101[2] | 17.20 |
| Igepal CO-850[3] | 17.20 |
| Igepal CO-890[4] | 17.20 |
| Igepal CO-977[5] | 24.57 |

[2]Ethylene Oxide adduct of nonyl phenol, a product of Rohm & Haas Corp.
[3]Ethylene Oxide adduct of nonyl phenol, a product of GAF Corporation.
[4]Ethylene Oxide adduct of nonyl phenol, a product of GAF Corporation.
[5]Ethylene Oxide adduct of nonyl phenol, a product of GAF Corporation.

| Monomer Charge | |
| --- | --- |
| Components | Parts |
| Ethyl Acrylate | 999.61 |
| Styrene | 689.40 |
| Acrylic Acid | 34.47 |
| Wet Adhesion Monomer of Example I | 34.47 |

The surfactant mix comprising deionized water, anionic surfactant and nonionic surfactants was fed into a five liter pre-emulsification tank at ambient temperature under nitrogen blanket with good agitation. The monomer charge was then added to the tank over 0.5 to 1.0 hour to produce a monomer pre-emulsion. A portion of the monomer pre-emulsion was added to the reactor charge, followed by the addition of the initiator charge. After agitation at reaction temperature for 26 to 30 minutes to allow the seed charge to polymerize completely, the remainder of the monomer-pre-emulsion was added over about 2 hours followed by an additional time of about 1 hour at reaction temperature.

The temperature was adjusted to 40° C. and a post add of 20.0 parts of dimethylethanolamine (DMEA) and 20.0 parts of deionized water followed by a chaser of 10.34 parts hydrogen peroxide (30 percent) and a chaser of 3.45 parts erythorbic acid and 46.55 parts of deionized water were added.

A coating composition was prepared from similar components according to the typical preparation described above in the specification, using the above described latex of the invention.

In wet adhesion evaluations, coatings made using the latex which were air dried for 24 hours at room temperature followed by 4 hours at 60° C. (24 hr. air dry/4 hr. 60° C.) exhibited 97% adhesion retention. Coatings made using the latex which were air dried for 4 days (4 days air dry) exhibited 100% adhesion retention.

EXAMPLE 3

Example 2 was repeated except that 1.0 percent of the wet adhesion monomer of Example 1 was used. The results of the wet adhesion evaluations were 97% adhesion retention (24 hr. air dry/4 hr. 60° C.) and 97% adhesion retention (4 days air dry).

COMPARISON EXAMPLE A

Example 2 was repeated except that no wet adhesion monomer of the invention was used. The results of the wet adhesion evaluation were 63% adhesion retention (24 hr. air dry/4 hr. 60° C.) and 0% adhesion retention (4 days air dry).

COMPARISON EXAMPLE B

A latex which is a commercial product of Rohm and Haas, marketed under the designation AC-64, was used to make a coating composition by the general procedure outlined in Example 2. The results of the wet adhesion evaluations were 93% adhesion retention (24 hr. air dry/4 hr. 60° C.) and 90% adhesion retention (4 days air dry).

COMPARISON EXAMPLE C

A latex which is a commercial product of Rohm and Haas, marketed under the designation AC-490, was used to make a coating composition by the general procedure of Example 2. The results of the wet adhesion evaluations were 63% adhesion retention (24 hr. air dry/4 hr. 60° C.) and 67% adhesion retention (4 days air dry).

EXAMPLE 4

Isocyanatoethyl methacrylate was reacted with 1-(beta-aminoethyl)-2-imidazolidone to form a wet adhesion monomer of the invention as follows:

To a one liter reaction vessel were charged the following components:

| Components | Parts |
|---|---|
| 1-(beta-aminoethyl)-2-imidazolidone | 50 |
| Toluene | 433.5 |

After reflux for about one-half hour to remove any water, the flask was cooled to 80° C. and one part methyl hydroquinone was added. Then over a period of about one half hour 60.1 parts ICEMA were added dropwise and the reaction vessel thereafter held at about 80° C. for about 1 hour to yield 112 grams of solid N-methacryloxyethyl ureido-N'-1-ethylene-2-imidazolidone wet adhesion monomer of the invention. A solution of 40 parts of this monomer in 60 parts of deionized water gave a wet adhesion monomer solution having a 39.05% solids content.

EXAMPLE 5

A latex was prepared, using the general procedure of Example 2, containing the wet adhesion monomer of Example 4 of the invention.

In a wet adhesion evaluation, coatings made using the latex according to the general procedure of Example 2 exhibited 94% wet adhesion retention (24 hr. air dry/4 hr. 60° C.).

COMPARISON EXAMPLE D

The latex of Example 5 was used without any wet adhesion monomer to prepare a coating composition according to the general procedure of Example 2.

The results of the wet adhesion evaluations were 40% adhesion retention (24 hr. air dry/4 hr. 60° C.) and 37% adhesion retention (4 days air dry).

EXAMPLE 6

Reaction of ICEMA and 1-(beta-aminoethyl)-2-imidazolidone to form a wet adhesion monomer of the invention.

To a 500 milliliter reaction vessel were charged the following components:

| Components | Parts |
|---|---|
| 1-(beta-aminoethyl)-2-imidazolidone | 25.83 |
| t-butanol | 47.32 |
| Methyl hydroquinone | 0.5 |

After heating the charge to the reaction temperature of 80° C., 31.03 parts ICEMA were fed to the reaction vessel over a time period of about one-third hour. After holding for one-half hour at reaction temperature, 167.5 parts deionized water were added to provide a wet adhesion monomer solution of the invention having 21.3% solids content.

EXAMPLE 7

Example 5 was repeated except that 2.0% of the wet adhesion monomer of Example 6 (161.83 parts) was substituted in the surfactant mix instead of the wet adhesion monomer of Example 4.

The wet adhesion evaluation, indicated a 93% wet adhesion retention (24 hr. air dry/60° C.).

EXAMPLES 8-16

In Examples 8-16 the wet adhesion monomer containing latexes of Examples 2, 5 and 7 were blended with various portions of the latex of comparison Example D. Examples 8, 9 and 10 contained the wet adhesion monomer of Example 2. Examples 11, 12 and 13 contained the wet adhesion monomer of Example 5 and Examples 14, 15 and 16 contained the wet adhesion monomer of Example 7. The wet adhesion evaluation of coatings prepared by the general procedure of Example 2 is shown in Table I below:

TABLE I

| Example | Percent by Weight of Latex with Wet Adhesion Monomers | Latex of Comparison Example D (Percent by Weight) | Percent by Weight of Wet Adhesion Monomer of Polymers | Wet Adhesion % Retention (24 hr. air dry/4 hr. 60° C.) | Wet Adhesion % Retention (4 days air dry) |
|---|---|---|---|---|---|
| 8 | 10 | 90 | 0.2 | 73 | 80 |
| 9 | 20 | 80 | 0.4 | 90 | 87 |
| 10 | 30 | 70 | 0.6 | 93 | 90 |
| 11 | 10 | 90 | 0.15 | 42 | |
| 12 | 20 | 80 | 0.3 | 60 | |
| 13 | 30 | 70 | 0.45 | 82 | |
| 14 | 10 | 90 | 0.2 | 64 | |
| 15 | 20 | 80 | 0.4 | 72 | |
| 16 | 30 | 70 | 0.6 | 81 | |

These results indicate that increasing the percentage by weight of wet adhesion monomers of the invention and, therefore, correspondingly decreasing the percentage by weight of the latex of Comparison Example D, leads to an increase in the wet adhesion retention of the coatings prepared with wet adhesion monomers of the invention.

COMPARISON EXAMPLE E-H

Finally, the latex of Comparison Example B, which performed the best in wet adhesion tests when compared with the materials of other Comparison Examples, was blended with various portions of the latex of Comparison Example D. The results shown below in Table II indicate that it was necessary to use 40 percent by weight of the of latex of Comparison Example B in order to achieve a wet adhesion retention of 90% or greater on the two wet adhesion retention tests, whereas as little as 30 percent by weight of the latex of Example 10 of the invention gave results of a wet adhesion retention of 90% or greater on the two wet adhesion retention tests.

TABLE II

| Comparison Example | Latex of Comparison Example B (Percent by Weight) | Latex of Comparison Example D (Percent by Weight) | Wet Adhesion % Retention (24 hr. air dry/4 hr. 60° C.) | Wet Adhesion % Retention (4 days air dry) |
|---|---|---|---|---|
| E | 10 | 90 | 60 | 37 |
| F | 20 | 80 | 67 | 33 |
| G | 30 | 70 | 80 | 20 |
| H | 40 | 60 | 93 | 90 |

We claim:

1. A compound having the formula:

$$RN\underset{\underset{O}{\overset{\|}{C}}}{\overset{(CR'_2)_m}{\diagup}}\hspace{-2pt}\diagdown N(CR'_2)_n X\overset{O}{\overset{\|}{C}}NHY$$

wherein
m is two or three;
n is an integer from one to four;
R is selected from the group consiting of:
  alkyl having one to six carbon atoms,
  hydrogen,
  $HOCH_2-$ and
  $R''O(CH_2)_a-$, wherein a is an integer from one to six and $R''$ is an alkyl having from 1 to 6 carbon atoms;
each R' in each $CR'_2$ unit of the $(CR'_2)_m$ group and of the $(CR'_2)_n$ group is independently selected from the group consisting of —H and alkyl having one to four carbon atoms;
X is selected from the group consisting of —O— and $$-\underset{\underset{H}{|}}{N}-;$$

and
Y is a free radical polymerizable unsaturated moiety selected from the group consisting of (meth)acrylic-containing monoisocyanate residues, styrene-containing monoisocyanate residues, maleic type monoisocyanate residues and fumaric type monoisocyanate residues.

2. The compound of claim 1 wherein Y is selected from the group consisting of:

$$-(CH_2)_q O \overset{O}{\overset{\|}{C}} \underset{R'''}{\overset{|}{C}}=CH_2,$$

[structure with $H_3CCCH_3$ and phenyl ring with $C=CH_2$ / $R'''$] and $$-CH_2CH_2O\overset{O}{\overset{\|}{C}}\underset{R'''}{\overset{|}{C}}=\underset{R'''}{\overset{|}{C}}\overset{O}{\overset{\|}{C}}OCH_2CH_3$$

wherein q is an integer from two to four and $R'''$ is selected from the group consisting of —H and —$CH_3$.

3. The compound of claim 2 having the formula:

$$RN\underset{\underset{O}{\overset{\|}{C}}}{\overset{(CR'_2)_m}{\diagup}}\hspace{-2pt}\diagdown N(CH_2)_n NH\overset{O}{\overset{\|}{C}}NH(CH_2)_q O\overset{O}{\overset{\|}{C}}\underset{R'''}{\overset{|}{C}}=CH_2$$

wherein m is two or three, n is an integer from one to four, q is an integer from two to four and $R'''$ is selected from the group consisting of —H and —$CH_3$.

4. The compound of claim 3 wherein said compound is N-methacryloxyethylureido-N'-(beta-ethyl)-2-imidazolidone.

5. A latex comprising the polymerization product of the compound having the formula:

$$RN\underset{\underset{O}{\overset{\|}{C}}}{\overset{(CR'_2)_m}{\diagup}}\hspace{-2pt}\diagdown N(CR'_2)_n X\overset{O}{\overset{\|}{C}}NHY$$

wherein
m is two or three;
n is an integer from one to four;
R is selected from the group consisting of:
  alkyl having one to six carbon atoms,
  hydrogen,
  $HOCH_2-$ and
  $R''O(CH_2)_a-$, wherein a is an integer from one to six and $R''$ is an alkyl having from 1 to 6 carbon atoms;
each R' in each $CR'_2$ unit of the $(CR'_2)_m$ group and of the $(CR'_2)_n$ group is independently selected from the group consisting of —H and alkyl having one to four carbon atoms;
X is selected from the group consisting of —O— and $$-\underset{\underset{H}{|}}{N}-;$$

and
Y is a free radical polymerizable unsaturated moiety selected from the group consisting of (meth)acrylic-containing monoisocyanate residues, styrene-containing monoisocyanate residues, maleic type monoisocyanate residues and fumaric type monoisocyanate residues and comonomers containing free radical polymerizable unsaturation.

6. The latex of claim 5 wherein the comonomers are selected from the group consisting of a polymerizable ethylenically unsaturated carboxylic acid, an alkyl (meth)acrylate wherein the alkyl group has from about 1 to about 20 carbon atoms, styrenes a vinyl carboxylate and mixtures thereof.

7. The latex of claim 6 wherein the comonomers comprise a polymerizable ethylenically unsaturated carboxylic acid and alkyl (meth)acrylate wherein the alkyl group has from about 1 to about 20 carbon atoms.

8. The latex of claim 6 wherein the comonomers comprise a polymerizable ethylenically unsaturated carboxylic acid, an alkyl (meth) acrylate wherein the alkyl group has from about 1 to about 20 carbon atoms and a styrene.

9. The latex of claim 6 wherein the comonomer comprise a vinyl carboxylate having 2 to 4 carbon atoms in the carboxylic moiety.

10. The latex of claim 5 wherein the compound having the formula:

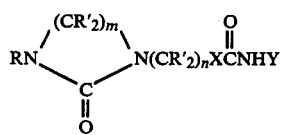

wherein
m is two or three;
n is an integer from one to four;
R is selected from the group consisting of:
alkyl having one to six carbon atoms,
hydrogen,
HOCH$_2$— and
R"O(CH$_2$)$_a$—, wherein a is an integer from one to six and R" is an alkyl having from 1 to 6 carbon atoms;
each R' in each CR'$_2$ unit of the (CR'$_2$)$_m$ group and of the (CR'$_2$)$_n$ group is independently selected from the group consisting of —H and alkyl having one to four carbon atoms;
X is selected from the group consisting of —O— and

and
Y is a free radical polymerizable unsaturated moiety selected from the group consisting of (meth)acrylic-containing monoisocyanate residues, styrene-containing monoisocyanate residues, maleic type monoisocyanate residues and fumaric type monoisocyanate residues is present in the latex in an amount of between 0.1 and 10 percent by weight based on the total weight of the comonomer present in the latex.

11. A coating composition comprising a latex comprising the polymerization produce of a compound having the formula:

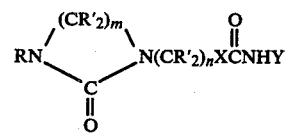

wherein
m is two or three;
n is an integer from one to four;
R is selected from the group consisting of;
alkyl having one to six carbon atoms,
hydrogen,
HOCH$_2$— and
R"O(CH$_2$)$_a$—, wherein a is an integer from one to six and R" is an alkyl having from 1 to 6 carbon atoms;
each R' in each CR'$_2$ unit of the (CR'$_2$)$_m$ group and the (CR'$_2$)$_n$ group is independently selected from the group consisting of —H and alkyl having one to four carbon atoms;
X is selected from the group consisting of —O— and

and
Y is a free radical polymerizable unsaturated moiety selected from the group consisting of (meth)acrylic-containing monoisocyanate residues, styrene-containing monoisocyanate residues, maleic type monoisocyanate residues and fumaric type monoisocyanate residues.

* * * * *

UNITED STATES PATENT AND TRADEMARK OFFICE
CERTIFICATE OF CORRECTION

PATENT NO. : 4,632,957

DATED : December 30, 1986

INVENTOR(S) : David A. Welsh et al

It is certified that error appears in the above-identified patent and that said Letters Patent is hereby corrected as shown below:

Column 11, line 38, claim 1; after "having" insert --from--.

Column 12, line 56, claim 5; after "having" insert --from--.

Column 13, line 20, claim 8; "(meth) acrylate" should read --(meth)acrylate--.

Column 13, line 23, claim 9; "comonomer" should read --comonomers--.

Column 13, line 51, claim 10; after "having" insert --from--.

Column 14, line 17, claim 11; "produce" should read --product--.

Column 14, line 38, claim 11; after "having" insert --from--.

Signed and Sealed this

Eighteenth Day of August, 1987

*Attest:*

DONALD J. QUIGG

*Attesting Officer*   *Commissioner of Patents and Trademarks*